US008614630B2

(12) United States Patent
Narasimhan et al.

(10) Patent No.: US 8,614,630 B2
(45) Date of Patent: Dec. 24, 2013

(54) FALL DETECTION USING SENSOR FUSION

(71) Applicant: Vital Connect, Inc., Campbell, CA (US)

(72) Inventors: Ravi Narasimhan, Sunnyvale, CA (US); Nima Ferdosi, San Jose, CA (US); Alexander Chan, Campbell, CA (US)

(73) Assignee: Vital Connect, Inc., Campbell, CA (US)

( * ) Notice: Subject to any disclaimer, the term of this patent is extended or adjusted under 35 U.S.C. 154(b) by 0 days.

(21) Appl. No.: 13/674,826

(22) Filed: Nov. 12, 2012

(65) Prior Publication Data
US 2013/0120147 A1 May 16, 2013

Related U.S. Application Data

(63) Continuation-in-part of application No. 13/296,139, filed on Nov. 14, 2011.

(51) Int. Cl.
G08B 23/00 (2006.01)
A61B 5/103 (2006.01)
G01C 9/00 (2006.01)
G06F 9/00 (2006.01)

(52) U.S. Cl.
USPC .............. 340/573.1; 340/539.11; 340/584; 600/595; 360/75; 702/141; 702/150; 726/12; 382/103

(58) Field of Classification Search
USPC .................................................. 340/573.1
See application file for complete search history.

(56) References Cited

U.S. PATENT DOCUMENTS

| 8,092,398 B2* | 1/2012 | Weinberg et al. ............ 600/595 |
| 2005/0067816 A1* | 3/2005 | Buckman .................. 280/730.1 |
| 2006/0001545 A1* | 1/2006 | Wolf ........................ 340/573.1 |
| 2006/0010340 A1* | 1/2006 | Makela et al. ..................... 714/5 |
| 2006/0268447 A1* | 11/2006 | Liao et al. ........................ 360/75 |
| 2008/0174444 A1 | 7/2008 | Noda et al. |
| 2009/0187370 A1 | 7/2009 | Pasolini et al. |
| 2010/0052896 A1* | 3/2010 | Goodman ................ 340/539.11 |
| 2010/0121226 A1* | 5/2010 | Ten Kate et al. ............. 600/595 |
| 2010/0121603 A1 | 5/2010 | Nyan et al. |
| 2010/0316253 A1* | 12/2010 | Yang et al. .................... 382/103 |
| 2011/0144542 A1 | 6/2011 | Jin et al. |
| 2011/0199216 A1 | 8/2011 | Flinsenberg et al. |

OTHER PUBLICATIONS

A.K. Bourke, et al., "Evaluation of a threshold-based tri-axial accelerometer fall detection algorithm", Gait & Posture 26 (2007), pp. 194-199.

M. Kangas, et al., "Determination of simple thresholds for accelerometry-based parameters for fall detection", Proceedings of the 29th Annual International Conference of the IEEE EMBS, Aug. 23-26, 2007, pp. 1367-1370.

International Search Report and Written Opinion of the International Searching Authority, International application No. PCT/US2012/064858, mailed Mar. 28, 2013.

* cited by examiner

Primary Examiner — Jennifer Mehmood
Assistant Examiner — Fekadeselassie Girma
(74) Attorney, Agent, or Firm — Sawyer Law Group, P.C.

(57) ABSTRACT

A method and system for fall detection using sensor fusion are disclosed. In a first aspect, the method comprises in response to any of first and second acceleration magnitude thresholds being satisfied, determining whether a height difference before and after impact of a fall satisfies a threshold and whether an angle threshold between an acceleration vector and a calibration vector is satisfied. In a second aspect, the system comprises a processing system and an application coupled to the processing system, wherein the application carries out the steps of the method.

19 Claims, 10 Drawing Sheets

| Figure 8A | Figure 8B |

Figure 8

FALL DETECTION USING SENSOR FUSION

CROSS-REFERENCE TO RELATED APPLICATION

This application is a continuation-in-part of U.S. patent application Ser. No. 13/296,139, filed Nov. 14, 2011, entitled "METHOD AND SYSTEM FOR FALL DETECTION OF A USER," which is incorporated herein by reference in its entirety.

FIELD OF THE INVENTION

The present invention relates to wireless sensor devices, and more particularly, to using a wireless sensor device to detect a user's fall.

BACKGROUND

Wireless sensor devices are used in a variety of applications including the health monitoring of users. In many of these health monitoring applications, a wireless sensor device is attached directly to the user's skin to measure certain data. This measured data can then be utilized for a variety of health related applications. In one instance, this measured data can be utilized to assist in detecting when a user has fallen due to a health related disease or external factor and is injured as a result.

Conventional approaches have detected when a user has fallen by measuring acceleration data related to the fall and comparing that data to various thresholds. However, these conventional approaches fail to discriminate problematic falls from activities of daily living, such as falling onto a couch to take a nap, and require that the wireless sensor device be attached to the user in specific orientations.

These issues limit the fall detection capabilities of wireless sensor devices. Therefore, there is a strong need for a cost-effective solution that overcomes the above issues by creating a method and system for a more accurate fall detection of a user without having to attach the wireless sensor device to the user in a specific and known orientation. The present invention addresses such a need.

SUMMARY OF THE INVENTION

A method and system for fall detection using sensor fusion are disclosed. In a first aspect, the method comprises in response to any of first and second acceleration magnitude thresholds being satisfied, determining whether a height difference before and after impact of a fall satisfies a threshold and whether an angle threshold between an acceleration vector and a calibration vector is satisfied.

In a second aspect, the system comprises a processing system and an application that is executed by the processing system. In response to any of first and second acceleration magnitude thresholds being satisfied, the application determines whether a height difference before and after impact of a fall satisfies a threshold and whether an angle threshold between an acceleration vector and a calibration vector is satisfied.

BRIEF DESCRIPTION OF THE DRAWINGS

The accompanying figures illustrate several embodiments of the invention and, together with the description, serve to explain the principles of the invention. One of ordinary skill in the art will recognize that the particular embodiments illustrated in the figures are merely exemplary, and are not intended to limit the scope of the present invention.

DETAILED DESCRIPTION OF PREFERRED EMBODIMENTS

Figure 1:
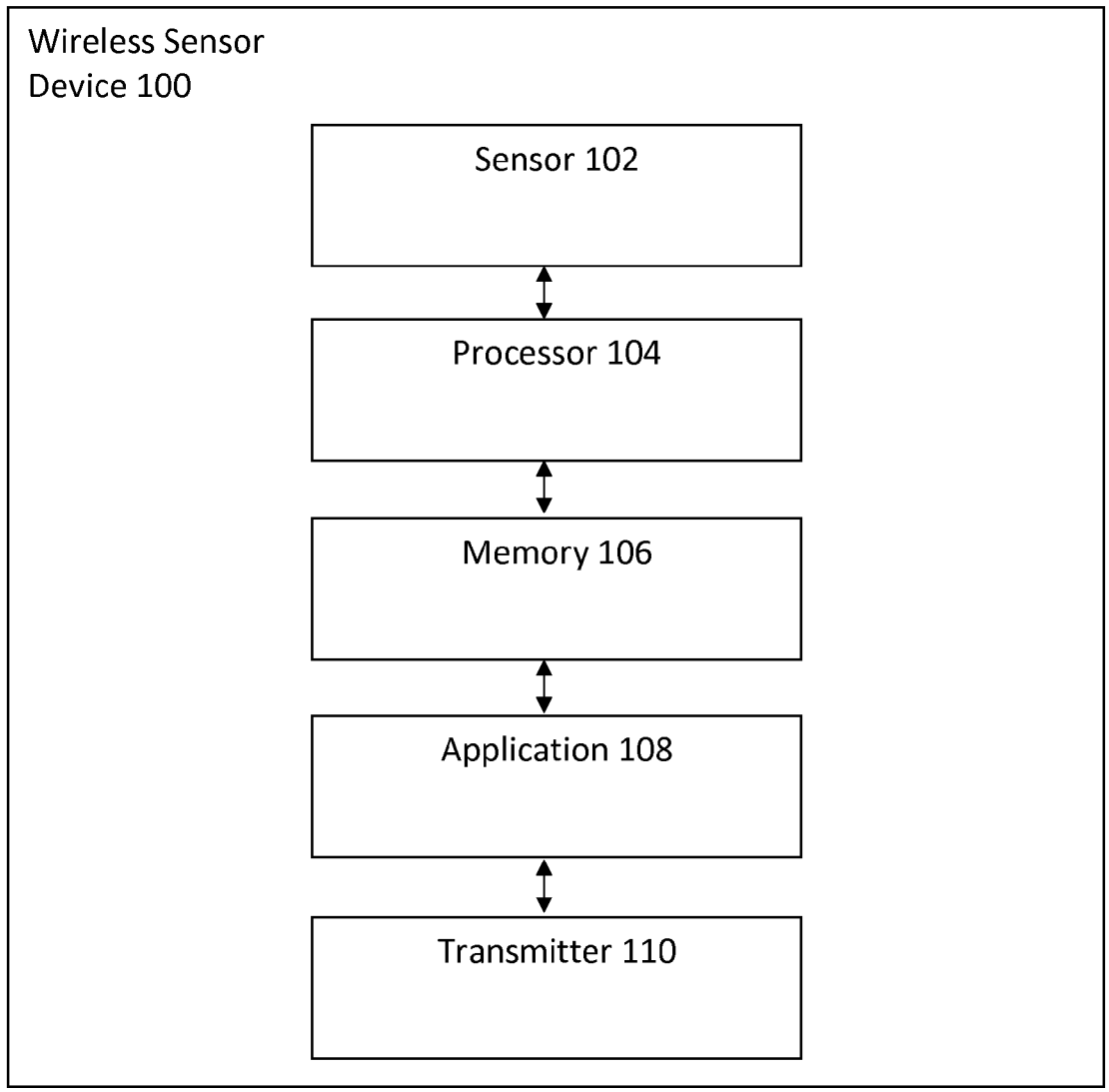
FIG. 1 illustrates a wireless sensor device in accordance with an embodiment.

The present invention relates to wireless sensor devices, and more particularly, to using a wireless sensor device to detect a user's fall. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

A method and system in accordance with the present invention allows for fall detection of a user using sensor fusion. By implementing a wireless sensor device that combines a tri-axial accelerometer and an altimeter to measure acceleration magnitudes and height differences, an efficient and cost-effective fall detection system is achieved that can discriminate problematic falls from activities of daily living and is accurate regardless of the attachment orientation of the wireless sensor device to the user. One of ordinary skill in the art readily recognizes that a variety of wireless sensor devices may be utilized and that would be within the spirit and scope of the present invention.

A user's fall is detectable if a magnitude of an acceleration vector is less than a threshold $A_l$ or greater than a threshold $A_h$. Using magnitude alone provides a smaller margin for threshold optimization to discriminate falls from activities of daily living. Additionally, a user's fall is detected if magnitude thresholds are satisfied and a Z-axis acceleration component present a few seconds later is nearly orthogonal to the acceleration vector due to gravity. Using the Z-axis acceleration component assumes that an accelerometer within the device is worn with Z-axis in the vertical direction which is not necessarily true with an accelerometer in a bandage form factored device that is attached to the user's chest in an unknown orientation.

Furthermore, using acceleration alone can lead to false positive/negative events in certain conditions including but not limited to crashing onto a bed, falling down stairs, and falling out of bed. Utilization of sensor fusion that features a combination of accelerometer measurements, wherein an acceleration magnitude is measured, and altimeter measurements, wherein a height difference before and after impact is measured, leads to a reduction in false positive/negative event rates.

To describe the features of the present invention in more detail, refer now to the following description in conjunction with the accompanying Figures.

In one embodiment, a wireless sensor device is attached to a user and continuously and automatically obtains data including but not limited to acceleration samples of the user. An application embedded within a processor of the wireless sensor device compares the acceleration samples to a lower acceleration magnitude threshold or to a higher magnitude threshold and then compares the acceleration samples to a calibration vector to determine whether a user has fallen and potentially been injured.

FIG. 1 illustrates a wireless sensor device 100 in accordance with an embodiment. The wireless sensor device 100 includes a sensor 102, a processor 104 coupled to the sensor 102, a memory 106 coupled to the processor 104, an application 108 coupled to the memory 106, and a transmitter 110 coupled to the application 108. The wireless sensor device 100 is attached, in any orientation, to a user. The sensor 102 obtains data from the user and transmits the data to the memory 106 and in turn to the application 108. The processor 104 executes the application 108 to determine information regarding whether a user has fallen. The information is transmitted to the transmitter 110 and in turn relayed to another user or device.

In one embodiment, the sensor 102 comprises both a microelectromechanical system (MEMS) tri-axial accelerometer and an altimeter and the processor 104 comprises a microprocessor. One of ordinary skill in the art readily recognizes that the wireless sensor device 100 can utilize a variety of devices for the sensor 102 including but not limited to any combination of uni-axial accelerometers, bi-axial accelerometers, gyroscopes, altimeters, and pressure sensors and that would be within the spirit and scope of the present invention. One of ordinary skill in the art readily recognizes that the wireless sensor device 100 can utilize a variety of devices for the processor 104 including but not limited to controllers and microcontrollers and that would be within the spirit and scope of the present invention. In addition, one of ordinary skill in the art readily recognizes that a variety of devices can be utilized for the memory 106, the application 108, and the transmitter 110 and that would be within the spirit and scope of the present invention.

Figure 2:
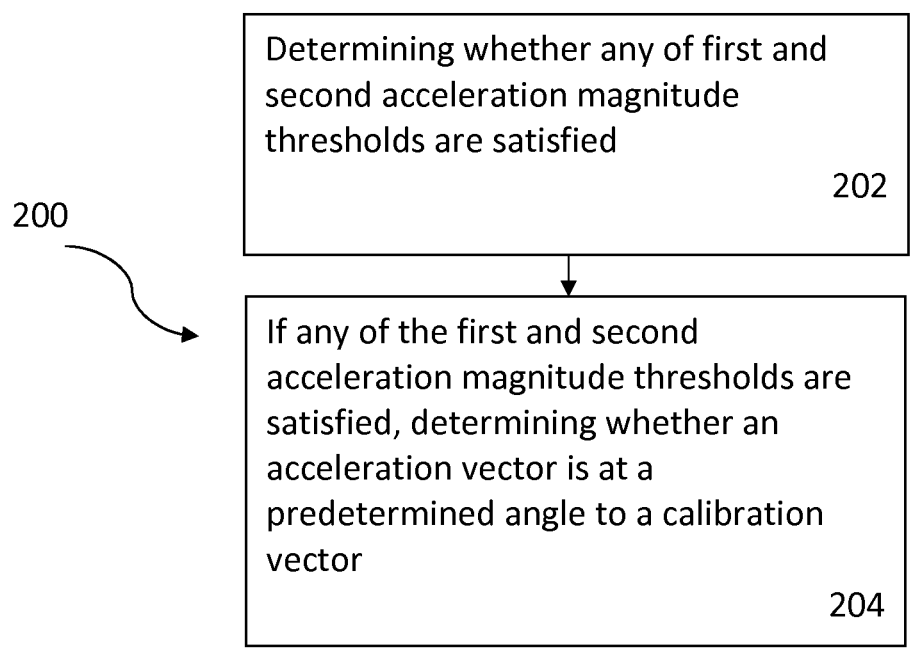
FIG. 2 illustrates a flow chart of a method for fall detection in accordance with an embodiment.

FIG. 2 illustrates a flow chart 200 of a method for fall detection in accordance with an embodiment. Referring to FIGS. 1 and 2 together, it is determined whether any of first and second acceleration magnitude thresholds of the sensor 102 are satisfied, via step 202. The sensor 102 is housed within the wireless sensor device 100. If the first or second acceleration magnitude thresholds of the sensor 102 are satisfied, it is determined whether an acceleration vector of a user of the sensor 102 is at a predetermined angle to a calibration vector, via step 204. One of ordinary skill in the art readily recognizes that a variety of predetermined angles can be utilized including but not limited to a nearly orthogonal angle and that would be within the spirit and scope of the present invention.

In one embodiment, if the first or second acceleration magnitude thresholds of the sensor 102 are satisfied and if the acceleration vector of the user of the sensor 102 is at the predetermined angle to the calibration vector, whether the user lacks movement for a predetermined time period is determined and notification information of the fall detection of the user is relayed to another user or device.

In one embodiment, step 202 includes obtaining an acceleration sample from the user and comparing the acceleration sample to a first acceleration magnitude threshold. In this embodiment, if the acceleration sample is less than the first acceleration magnitude threshold, the first acceleration magnitude threshold of the sensor 102 is satisfied. If not, step 202 further includes comparing the acceleration sample to a second acceleration magnitude threshold. If the acceleration sample is greater than the second acceleration magnitude threshold, the second acceleration magnitude threshold of the sensor 102 is satisfied.

In one embodiment, step 204 includes attaching in any orientation, including but not limited to along the X-axis, Y-axis, and Z-axis, the wireless sensor device 100 to the user and determining the calibration vector. The calibration vector is an acceleration vector when the user is in a vertical position, including but not limited to sitting upright or standing. Once the calibration vector is determined, at least one acceleration sample is obtained from the user using the wireless sensor device 100 and the at least one acceleration sample is compared to the calibration vector. If the at least one acceleration sample is nearly orthogonal to the calibration vector, then the fall of the user is detected.

Figure 3:
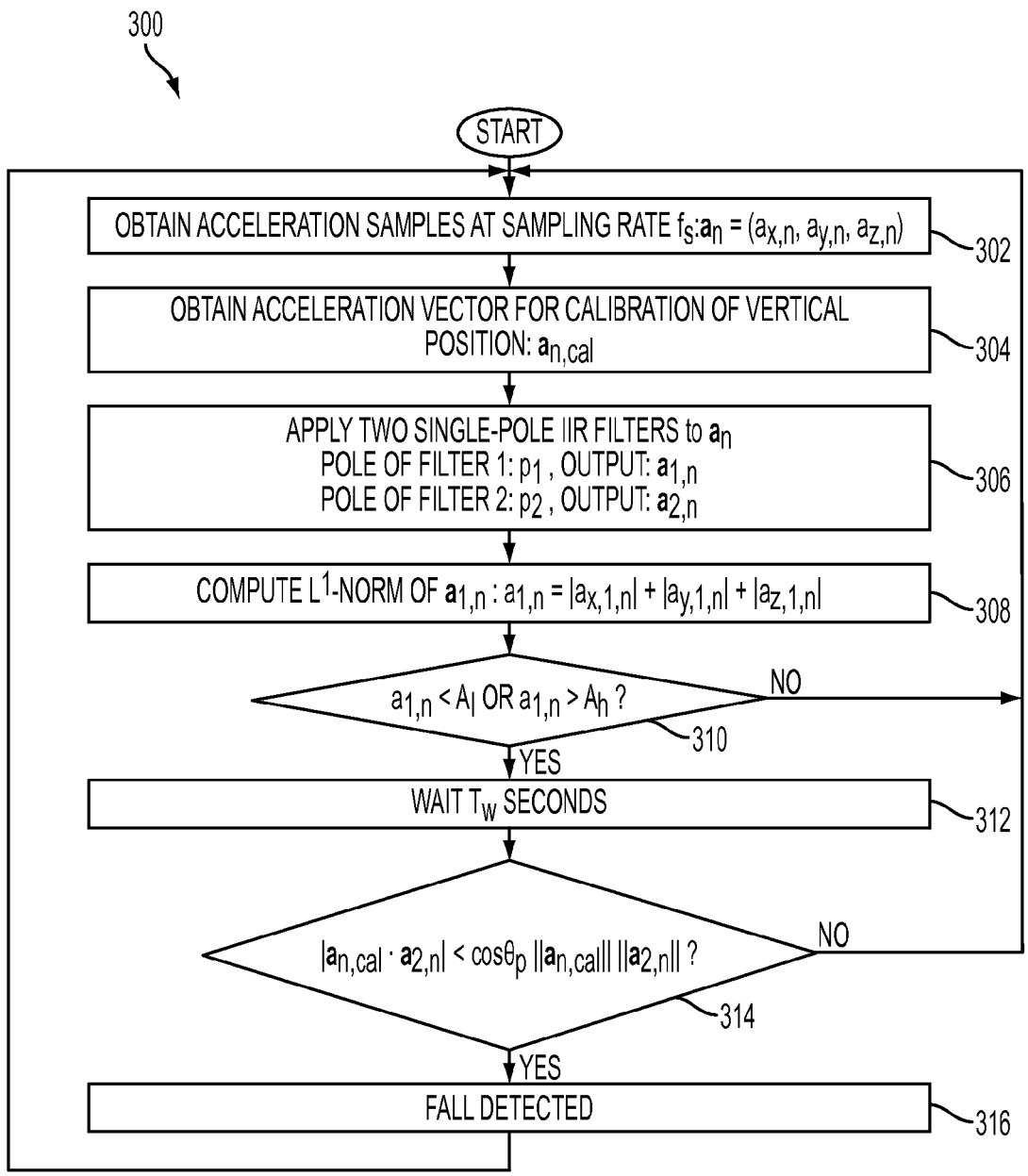
FIG. 3 illustrates a more detailed flow chart of a method for fall detection in accordance with a first embodiment.

FIG. 3 illustrates a more detailed flowchart 300 of a method for fall detection in accordance with a first embodiment. In this embodiment, acceleration samples ($a_n$) are obtained from a user of the wireless sensor device 100 at a sampling rate ($f_s$), via step 302. One of ordinary skill in the art readily recognizes that a variety of acceleration sample ranges can be utilized including but not limited to +−4 gravitational acceleration (g) and that would be within the spirit and scope of the present invention. In addition, one of ordinary skill in the art readily recognizes that a variety of sampling rates ($f_s$) can be utilized including but not limited to 60 Hertz (Hz), 100 Hz, and 500 Hz and that would be within the spirit and scope of the present invention. The acceleration samples ($a_n$) can be represented by the following equation:

$$a_n = (a_{x,n}, a_{y,n}, a_{z,n}). \quad (1)$$

After obtaining the acceleration samples ($a_n$), an acceleration vector ($a_{n,cal}$) is obtained for the calibration of the vector position, via step 304. The acceleration vector ($a_{n,cal}$) is a calibration vector. One of ordinary skill in the art readily recognizes that a variety of calibration methodologies for obtaining the calibration vector can be utilized and that would be within the spirit and scope of the present invention. In one embodiment, the wireless sensor device 100 is attached when the user is in a vertical position and then an acceleration sample is measured immediately after the attachment. In this embodiment, the measured acceleration sample is determined to be the calibration vector.

In another embodiment, a pedometer type device is integrated into the wireless sensor device 100 to detect user footsteps. After the wireless sensor device 100 is attached to the user in any horizontal or vertical position, including but not limited to laying down or standing, an acceleration sample is measured immediately after the user takes at least one footstep or is walking. In this embodiment, the measured acceleration sample is determined to be the calibration vector.

Two filters are applied to the acceleration sample ($a_n$) to output vector $a_{1,n}$ from the pole of the first filter (filter 1) and to output vector $a_{2,n}$ from the pole of the second filter (filter 2), via step 306. One of ordinary skill in the art readily recognizes that a variety of filters can be utilized for the two filters including but not limited to single-pole infinite impulse response (IIR) filters, multiple-pole IIR filters, finite impulse response (FIR) filters, median filters, high-pass filters and low-pass filters and that would be within the spirit and scope of the present invention. In one embodiment, the first filter (filter 1) is a single-pole infinite impulse response filter that resembles a high-pass filter with a pole of $p_1=1-1/8$ and the second filter (filter 2) is a single-pole infinite impulse response filter that resembles a low-pass filter with a pole of $p_2=1-1/50$.

$L^1$-norm of the output vector $a_{1,n}$ is computed, via step 308, which can be represented by the following equation:

$$a_{1,n}=|a_{x,1,n}|+|a_{y,1,n}|+|a_{z,1,n}|. \quad (2)$$

The $L^1$-norm computation of the output vector $a_{1,n}$ results in a scalar $a_{1,n}$ which is compared to a lower acceleration magnitude threshold ($A_l$) or to a higher acceleration magnitude threshold ($A_h$), via step 310. One of ordinary skill in the art readily recognizes that a variety of $L^p$-norm computations can be utilized including but not limited to $L^1$-norm, $L^2$-norm, and $L^\infty$-norm and that would be within the spirit and scope of the present invention.

In addition, one of ordinary skill in the art readily recognizes that a variety of mathematical calculations can be utilized to convert an output vector into a scalar and that would be within the spirit and scope of the present invention. One of ordinary skill in the art readily recognizes that a variety of acceleration magnitude thresholds can be utilized and that would be within the spirit and scope of the present invention. In one embodiment, the lower acceleration magnitude threshold ($A_l$) is 0.3 g and the higher acceleration magnitude threshold ($A_h$) is 3.5 g.

If the condition in step 310, either $a_{1,n}<A_l$ or $a_{1,n}>A_h$, is satisfied, then a predetermined time period ($T_w$) is waited, via step 312. One of ordinary skill in the art readily recognizes that the predetermined time period may encompass a variety of time periods including but not limited to 2 to 5 seconds and that would be within the spirit and scope of the present invention. If the condition in step 310 is not satisfied, then additional acceleration samples ($a_n$) are obtained, via step 302.

After waiting the predetermined time period ($T_w$), it is determined whether the output vector $a_{2,n}$ is at a predetermined angle ($\square_p$), including but not limited to 60 degrees and a nearly orthogonal angle, to the acceleration vector for calibration of vertical position ($a_{n,cal}$), via step 314. This determination can be represented by the following equation:

$$|a_{n,cal} \cdot a_{2,n}| < \cos \square_p \|a_{n,cal}\| \|a_{2,n}\|. \quad (3)$$

If equation (3) is satisfied, then a user's fall is detected, via step 316 and additional acceleration samples ($a_n$) are obtained, via step 302. If equation (3) is not satisfied, additional acceleration samples ($a_n$) are obtained, via step 302.

Figure 4:
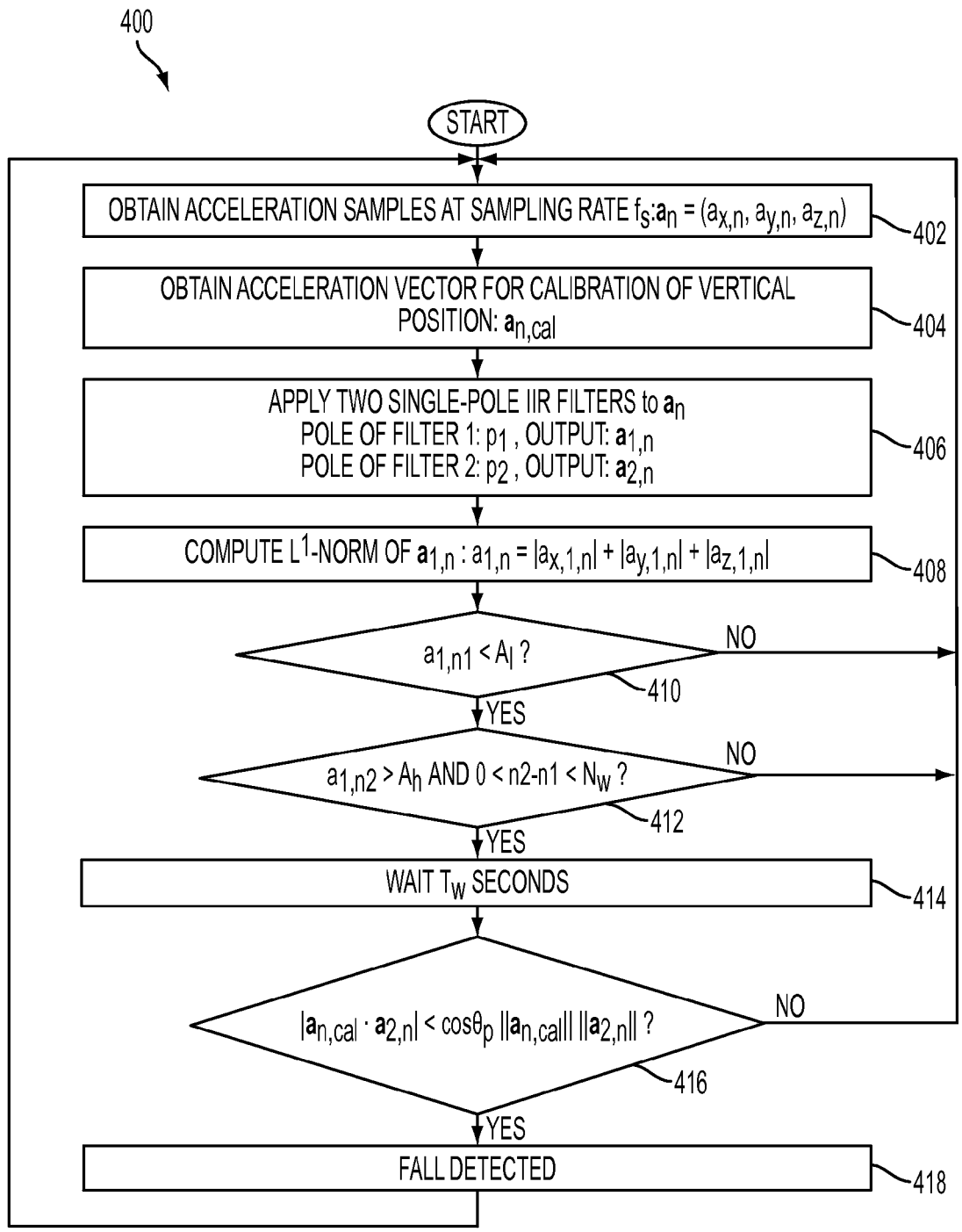
FIG. 4 illustrates a more detailed flow chart of a method for fall detection in accordance with a second embodiment.

In one embodiment, the $L^1$-norm computation of the output vector $a_{1,n}$ that results in a scalar $a_{1,n}$ is compared to both a lower acceleration magnitude threshold ($A_l$) and also to a higher acceleration magnitude threshold ($A_h$). FIG. 4 illustrates a more detailed flowchart 400 of a method for fall detection in accordance with a second embodiment. Referring to FIG. 3 and FIG. 4 together, steps 402-408, which are similar to steps 302-308, are performed. After steps 402-408 are performed, scalar $a_{1,n}1$ is compared to a lower acceleration magnitude threshold ($A_l$), via step 410. If the condition in step 410, $a_{1,n}1<A_l$, is not satisfied, then additional acceleration samples ($a_n$) are obtained, via step 302.

If the condition in step 410 is satisfied, scalar $a_{1,n}2$ is compared to a higher acceleration magnitude threshold ($A_h$) within a predetermined sampling number ($N_w$), via step 412. One of ordinary skill in the art readily recognizes that the predetermined sampling number ($N_w$) could include a varying number of acceleration samples and that would be within the spirit and scope of the present invention. If the condition in step 412, $a_{1,n}>A_h$ and $0<n2-n1<N_w$, is not satisfied, then additional acceleration samples ($a_n$) are obtained, via step 302. Referring to FIG. 3 and FIG. 4 together, if the condition in step 412 is satisfied, steps 414-418, which are similar to steps 312-316, are performed.

After an injurious fall, most individuals are in a horizontal position. Thus, a main feature of the method and system for fall detection of a user is a fall detection algorithm capable of identifying the user's horizontal position after a potential injurious impact. The combination of impact and horizontal position detection provides increased sensitivity and specificity in the fall detection of an individual. Furthermore, because most individuals lie on the floor for a significant amount of time after a potential injurious impact, the fall detection algorithm integrates the requirement of a low activity level of the user several seconds after the potential injurious impact to decrease false positives.

One of ordinary skill in the art readily recognizes that the low activity level can be determined by a variety of methodologies including but not limited to an activity metric that is defined as a moving average of the $L^1$-norm of a band-pass filtered acceleration vector and that would be within the spirit and scope of the present invention. Additionally, one of ordinary skill in the art readily recognizes that a horizontal position of the user can be determined by a variety of methodologies including but not limited to computing an angle of an acceleration vector shortly after an impact with an acceleration vector obtained when the user was in a vertical position.

In order to compute the angle of the acceleration vector shortly after the impact and provide flexibility in the wireless sensor device placement and orientation on the torso of the user, a calibration procedure is utilized to determine the vertical acceleration vector before the fall detection algorithm is executed. One of ordinary skill in the art readily recognizes that several calibration methods can be utilized including but not limited to implicit calibration by measuring the acceleration vector when the user is walking, explicit calibration involving the user notifying a system (e.g., using a mobile phone) when he or she is in a vertical position and that would be within the spirit and scope of the present invention.

If the user has a stooped posture, the fall detection algorithm disregards the user's horizontal position and utilizes impact alone for the fall detection. One of ordinary skill in the art readily recognizes that a stooped posture can include a variety of postures including but not limited to a posture inferred if the magnitude of a z-axis component of the acceleration vector measured during calibration is greater than a threshold and that would be within the spirit and scope of the present invention.

Figure 5:
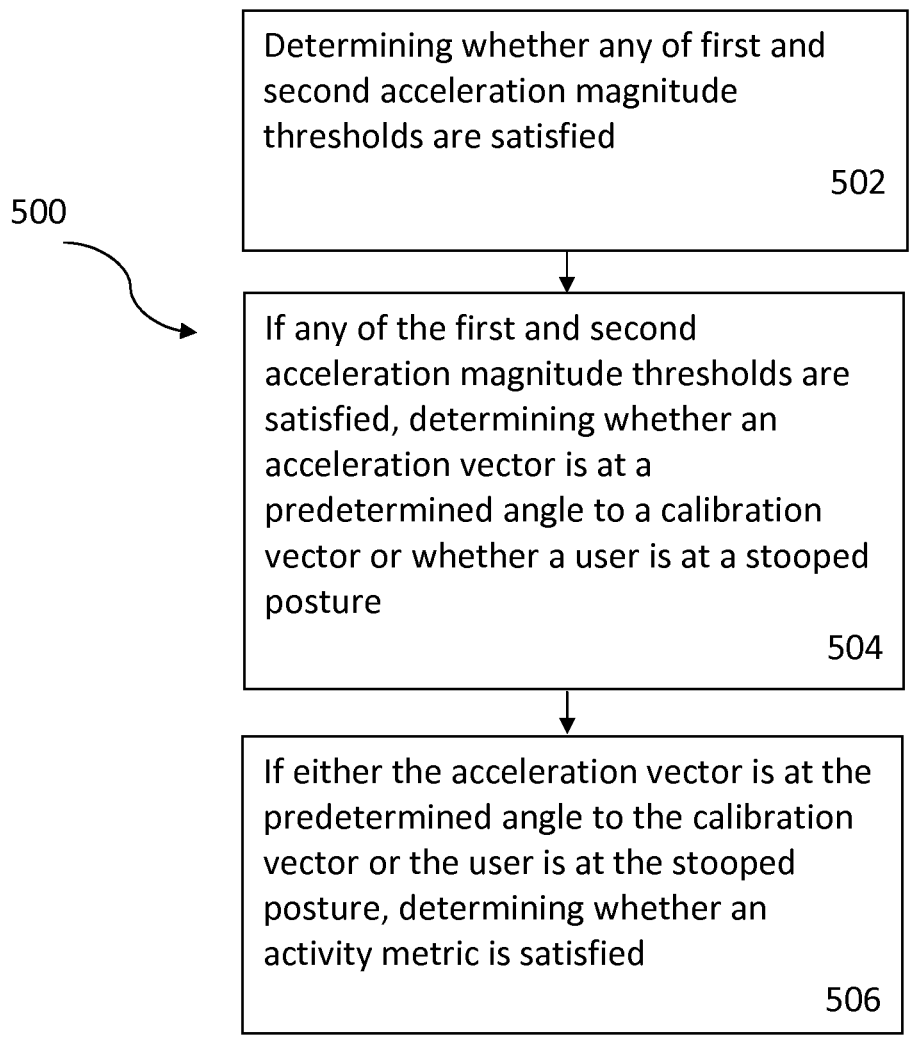
FIG. 5 illustrates a flow chart of a method for fall detection using an activity metric in accordance with an embodiment.

FIG. 5 illustrates a flow chart 500 of a method for fall detection using an activity metric in accordance with an embodiment. Referring to FIGS. 1 and 5 together, it is determined whether any of first and second acceleration magnitude thresholds of the sensor 102 are satisfied, via step 502. The sensor 102 is housed within the wireless sensor device 100. If the first or second acceleration magnitude thresholds of the sensor 102 are satisfied, it is determined whether an acceleration vector of a user of the sensor 102 is at a predetermined angle to a calibration vector or whether a user of the sensor 102 is at a stooped posture, via step 504. If the acceleration vector of the user is at the predetermined angle to the calibration vector or if the user is at the stooped posture, it is determined whether an activity metric is satisfied, via step 506.

One of ordinary skill in the art readily recognizes that a variety of predetermined angles can be utilized including but not limited to a nearly orthogonal angle and that would be within the spirit and scope of the present invention. Additionally, one of ordinary skill in the art readily recognizes that a variety of methodologies for determining whether the user is at the stooped posture can be utilized and that would be within the spirit and scope of the present invention.

Figure 6:
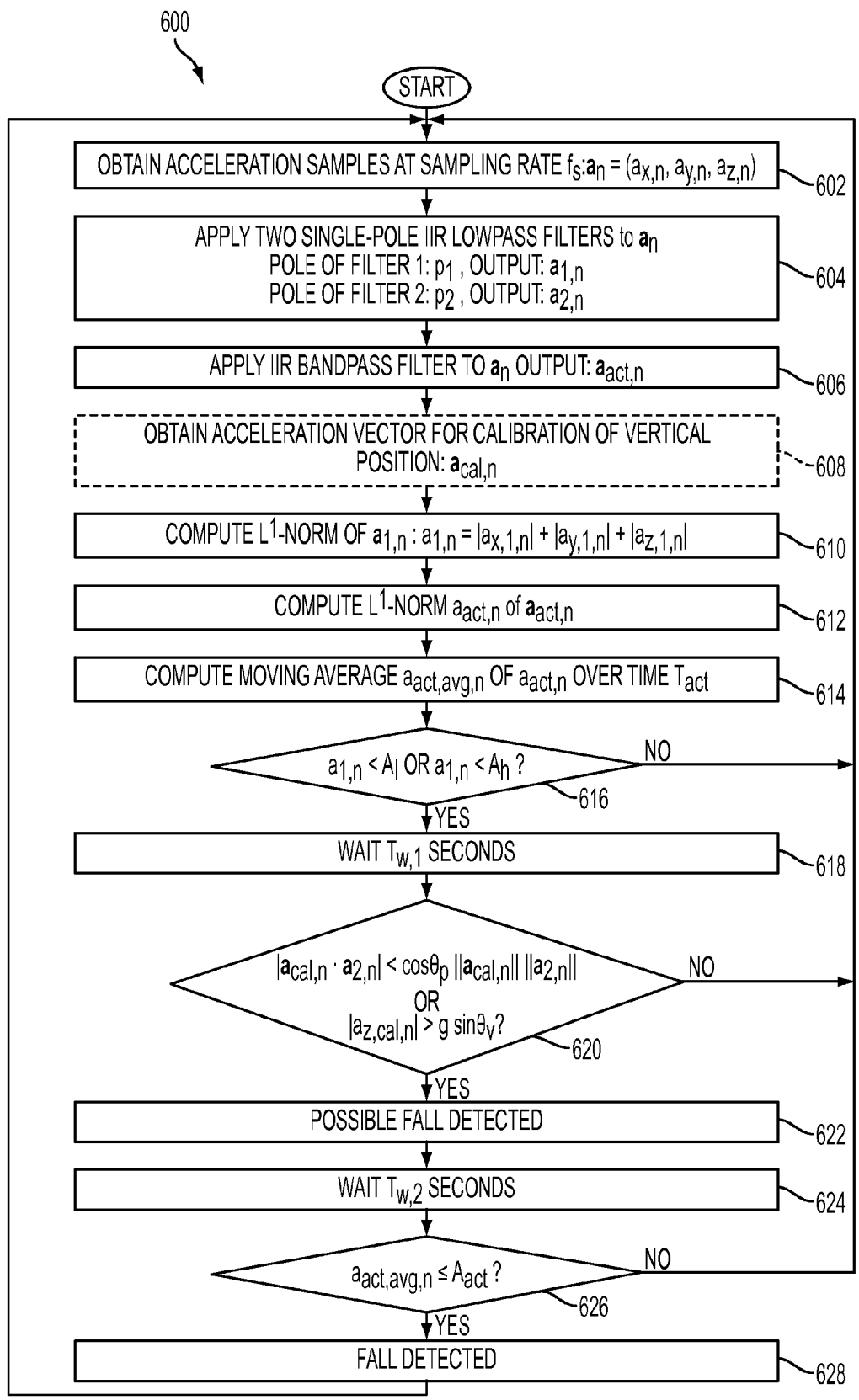
FIG. 6 illustrates a more detailed flow chart of a method for fall detection using an activity metric in accordance with an embodiment.

FIG. 6 illustrates a more detailed flowchart 600 of a method for fall detection using an activity metric in accordance with an embodiment. The more detailed flowchart 600 is of a fall detection algorithm located within the wireless sensor device 100. Referring to FIG. 4 and FIG. 6 together, steps, 602, 604, 608, and 610, which are similar to steps 402, 406, 404, and 408 respectively, are performed. In one embodiment, an acceleration vector $a_n=(a_{x,n}, a_{y,n}, a_{z,n})$ consisting of the x, y, and z components is obtained from a user of the wireless sensor device 100 at the $n^{th}$ time instant with a sampling rate $(f_s)$ of 125 Hz using the tri-axial accelerator located within the wireless sensor device 100, via step 602.

In this embodiment, the acceleration vector $a_n$ is passed through two single-pole IIR low-pass filters with poles $p_1=13.8$ Hz and $p_2=0.8$ Hz to produce vectors $a_{1,n}$ and $a_{2,n}$, via step 604. Vector $a_{1,n}$ is used to track large changes in acceleration from impacts and vector $a_{2,n}$, which contains only very low frequencies, is used to obtain stable measurements for horizontal position determination. One of ordinary skill in the art readily recognizes that the poles of the IIR low-pass filters can be a variety of values and that would be within the spirit and scope of the present invention.

In between steps 604 and 608, an IIR band-pass filter is further applied to $a_n$ to produce a vector $a_{act,n}$, which is a measure of an activity level of the user, via step 606. One of ordinary skill in the art readily recognizes that a variety of IIR band-pass filters can be utilized including but not limited to a sixth-order elliptic filter with a passband ripple of 0.1 decibel (dB), a stopband attenuation of 100 dB, and a passband of 0.25 Hz to 20 Hz and that would be within the spirit and scope of the present invention.

During the initialization of the fall detection algorithm, a calibration vector $a_{cal,n}$ is obtained using the vector $a_{2,n}$, via step 608. In continuous operation, the $L^1$-norm of vector $a_{1,n}$ is computed, via step 610, as follows:

$$a_{1,n}=\|a_{1,n}\|_1=|a_{x,1,n}|+|a_{y,1,n}|+|a_{z,1,n}| \quad (4)$$

For the activity level of the user, the $L^1$-norm $a_{act,n}$ of $a_{act,n}$ is computed, via step 612. The computed $L^1$-norm $a_{act,n}$ is utilized to further compute a moving average of $a_{act,n}$ over a time period $(T_{act})$, or $a_{act,avg,n}$, where $a_{act,avg,n}$ is also defined as the activity metric, via step 614. An impact is detected if the $L^1$-norm $a_{1,n}$ is less than a first threshold $A_l$ or greater than a second threshold $A_h$, via step 616. More specifically, the first threshold condition $(a_{1,n}<A_l)$ detects the occurrence of a near "free fall" motion of the user before impact while the second threshold condition $(a_{1,n}>A_h)$ detects the large acceleration caused by the impact of the user falling to the ground.

In this embodiment, if an impact is detected, the fall detection algorithm waits for a time period $(T_{w,1}$ seconds), via step 618. After waiting $T_{w,1}$ seconds, the horizontal position criterion is determined. The user is determined to be in a horizontal position if the angle between the calibration vector $a_{cal,n}$ and vector $a_{2,n}$ is larger than $\theta_p$, via step 620, where the $L^2$-norm of $a_n$ is given by $\|a_n\|_2=(a_{x,n}^2+a_{y,n}^2+a_{z,n}^2)^{1/2}$, per the following equation:

$$|a_{cal,n}\cdot a_{2,n}|<\cos\theta_p \|a_{cal,n}\|\|a_{2,n}\| \quad (5)$$

As aforementioned, the horizontal position criterion is ignored if a stooped posture of the user is detected during calibration, also via step 620, per the following equation:

$$|a_{z,cal,n}|>g\sin\theta_v \quad (6)$$

Accordingly, a possible fall of the user is detected via step 622 if both the impact criteria (via step 616) are satisfied and either the horizontal position criterion is satisfied or a stooped posture is detected during calibration (via step 620). If a possible fall is detected, the fall detection algorithm waits for a second time period $(T_{w,2}$ seconds), via step 624. After waiting $T_{w,2}$ seconds, the activity criterion comparing $a_{act,avg,n}$ to a predetermined $A_{act}$ value is checked, via step 626.

If the activity criterion is not satisfied, or $a_{act,avg,n}>A_{act}$, the user was active and likely unharmed after the possible fall; thus, the possible fall is not upgraded to an actual determined fall. However, if the activity criterion is satisfied, or $a_{act,avg,n}\leq A_{act}$, the user was not active and likely harmed after the possible fall; thus, the possible fall is upgraded to an actual determined fall, via step 628.

After an actual determined fall is detected by the fall detection algorithm of method 600, one of ordinary skill in the art readily recognizes that a variety of notification measures can be taken to ensure the safety of the user including but not limited to notifying a monitoring system, another user, the police, and the medical authorities and that would be within the spirit and scope of the present invention.

One of ordinary skill in the art readily recognizes that typical parameter values for the fall detection algorithm of method 600 can be a variety of values including but not limited to $A_l=0.3$ g, $A_h=3.0$ g, $A_{act}=0.2$ g, $\theta_p=60°$, $\theta_v=20°$, $T_{w,1}=2$ s, $T_{w,1}=60$ s, and $T_{act}=1$ s and that would be within the spirit and scope of the present invention.

Figure 7:
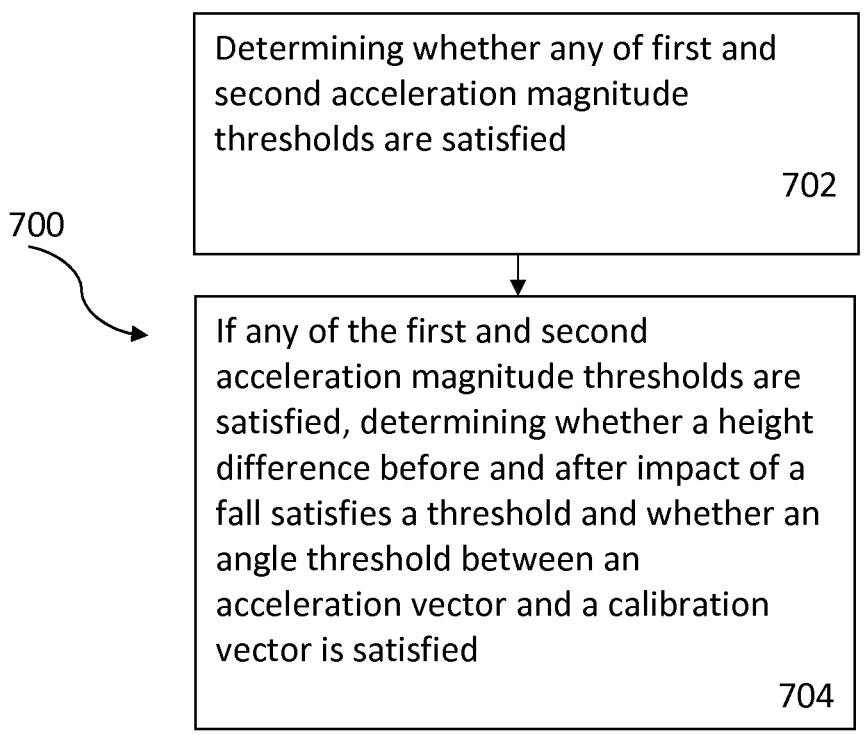
FIG. 7 illustrates a flow chart of a method for fall detection using sensor fusion in accordance with an embodiment.

FIG. 7 illustrates a flow chart 700 of a method for fall detection using sensor fusion in accordance with an embodiment. Referring to FIGS. 1 and 7 together, it is determined whether any of first and second acceleration magnitude thresholds are satisfied, via step 702. If any of the first and second acceleration magnitude thresholds are satisfied, it is determined whether a height difference before and after impact of a fall satisfies a threshold and whether an angle threshold between an acceleration vector and a calibration vector is satisfied, via step 704.

Figure 8A:
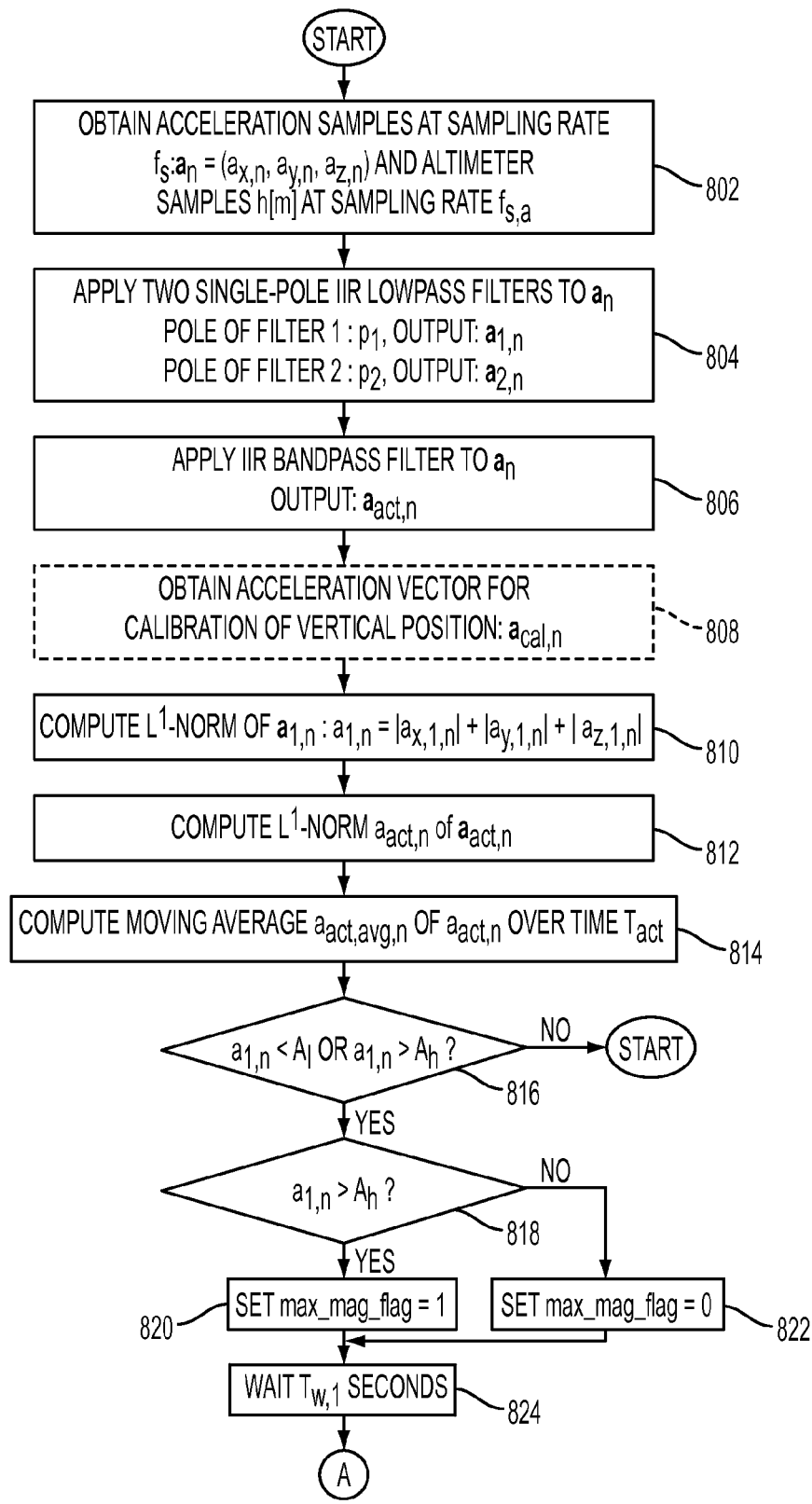
FIG. 8 illustrates a more detailed flow chart of a method for fall detection using sensor fusion in accordance with an embodiment.
Figure 8B:
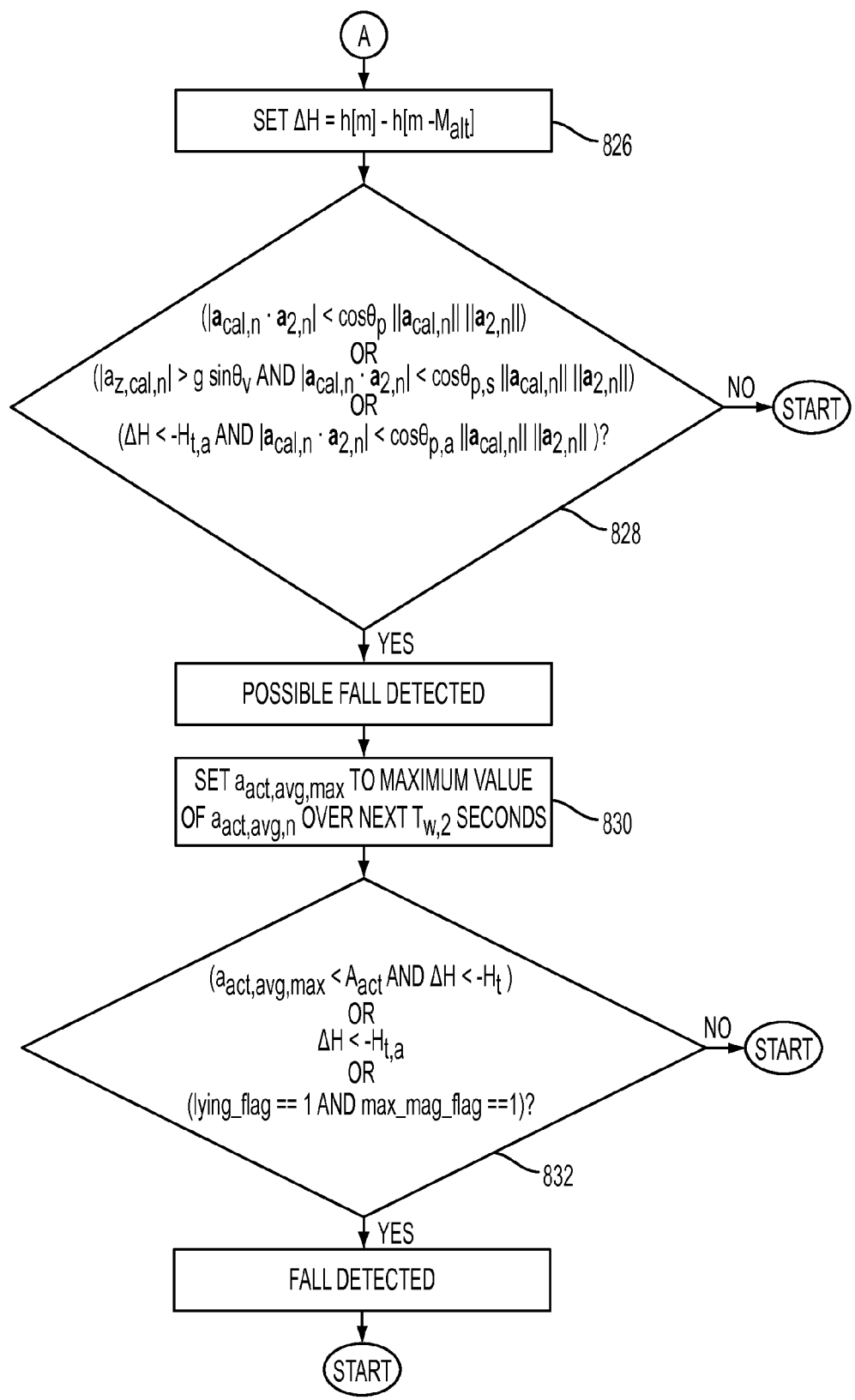

FIG. 8 illustrates a more detailed flow chart 800 of a method for fall detection using sensor fusion in accordance with an embodiment. The more detailed flowchart 800 is of a fall detection algorithm that utilizes sensor fusion and is located within the wireless sensor device 100. Referring to FIG. 6 and FIG. 8 together, steps 802 through 816, which are similar to steps 602 through 614 respectively, are performed. Altimeter samples h[m] are additionally obtained at a sampling rate of $f_{s,a}$, via step 802.

In one embodiment, the fall detection algorithm determines whether $a_{1,n}$ is greater than $A_h$, via step 818. If $a_{1,n}$ is greater than $A_h$ then max_mag_flag is set to 1, via step 820, and if not, then max_mag_flag is set to 0, via step 822. The purpose of the max_mag_flag is to identify an impact when detecting a fall from an initial horizontal posture, for example a fall out of bed. After setting the max_mag_flag, the fall detection algorithm waits for a predetermined time period including but not limited to $T_{w,1}$ seconds, via step 824, and sets a height difference as $\Delta H=h[m]-h[m-M_{alt}]$, via step 826.

After determining that magnitude thresholds are satisfied $(a_{1,n}<A_l$ or $a_{1,n}>A_h)$ via step 816 and after setting the height difference via step 826, the fall detection algorithm detects a possible fall, via step 828. A possible fall is detected if:

the acceleration vector is nearly orthogonal based on an angle threshold to the calibration vector via aforementioned equation 5;

a stooped posture of the user is detected via aforementioned equation 6 and a second angle threshold between the acceleration vector $(a_{2,n})$ and calibration vector $(a_{cal,n})$ is satisfied via $|a_{cal,n}\cdot a_{2,n}|<\cos\square_{p,s}\|a_{n,cal}\|\|a_{2,n}\|$; or a height difference measured by the altimeter before and after impact satisfies a threshold via $\Delta H<-H_{t,a}$ (to detect falling down stairs) and a third angle between the acceleration vector and calibration vector is satisfied via $|a_{cal,n} \cdot a_{2,n}| < \cos \Box_{p,a} \|a_{n,cal}\| \|a_{2,n}\|$.

If a possible fall is detected via step 828, $a_{act,avg,max}$ is set as the maximum value of activity metric $a_{act,avg,n}$ over a predetermined time period of the next $T_{w,2}$ seconds, via step 830.

After setting the maximum value of the activity metric via step 830, the fall detection algorithm confirms that a fall has occurred, via step 832. A fall is confirmed if:

a maximum value of the activity metric a predetermined time period after the possible fall is less than a threshold via $a_{act,avg,max} < A_{act}$ and a height difference measured by the altimeter before and after impact satisfies a threshold via $\Delta H < -H_t$;

a height difference measured by the altimeter before and after impact satisfies another threshold that covers a fall down stairs via $\Delta H < -H_{t,a}$; or the user is lying down for a predetermined time period of $T_{lie}$ seconds via lying_flag=1 and an acceleration magnitude is greater than a threshold that covers a fall out of bed via max_mag_flag=1.

In one embodiment, when a lying posture is detected for at least $T_{lie}$ seconds, lying_flag is set to 1 and $A_h$ is set to $A_{h,lie}$, and if a lying posture is not detected for at least $T_{lie}$ seconds, lying_flag is set to 0 and $A_h$ is set to $A_{h,normal}$.

The parameters of the fall detection algorithm of FIG. 8 include filter parameters, acceleration thresholds, angular thresholds, temporal thresholds, and height thresholds. In one embodiment, the filter parameters include but are not limited to lowpass filter pole $p_1$=13.8 Hz, lowpass filter pole $p_2$=0.2 Hz (function of $T_{w,1}$), and digital bandpass filter with denominator coefficient vector A=[1024, −992, 32], numerator coefficient vector B=[496, 0, −496], sampling rate $f_s$=62.5 Hz. In one embodiment, the acceleration thresholds include but are not limited to $A_l$=0.3 g (low threshold), $A_{h,normal}$=3.0 g (high threshold in normal operation), $A_{h,lie}$=2.0 g (high threshold for lying posture), and $A_{act}$=0.2 g (activity threshold to confirm fall).

In one embodiment, the angular thresholds include but are not limited to $\Box_p$=60° (horizontal position criterion, 90°→perpendicular to calibration vector), $\Box_v$=30° (stooped threshold, 0° means completely vertical), $\Box_{p,s}$=40° (horizontal position criterion when stooped, 90°→perpendicular to calibration vector), and $\Box_{p,a}$=0° (horizontal position criterion for stairs, 90°→perpendicular to calibration vector).

In one embodiment, the temporal thresholds include but are not limited to $T_{w,1}$=4 seconds (waiting time after impact), $T_{w,2}$=20 seconds (waiting time after possible fall), $T_{act}$=1 second (activity metric averaging time), $M_{alt}$=$T_{alt}$*$f_{s,a}$ where $T_{alt}$=$T_{w,1}$+2 seconds and $f_{s,a}$=4 Hz (time in samples for height difference), and $T_{lie}$=20 seconds (time for lying down before lying_flag is set to 1). In one embodiment, the height thresholds include but are not limited to $H_t$=0.5*height of user (height threshold to confirm fall) and $H_{t,a}$=2 meters (height threshold for fall from stairs).

Accordingly, a possible fall is detected by the wireless sensor device 100 if magnitude thresholds are satisfied and any of the following are satisfied: a) an acceleration vector after a predetermined time period (e.g. a few seconds) is nearly orthogonal based on an angle thresholds to the calibration vector, b) a stooped posture of the user is detected and a second angle threshold between and an acceleration vector and a calibration vector is satisfied, or c) a height difference measured by the altimeter before and after impact satisfies a threshold and a third angle threshold between acceleration vector and calibration vector is satisfied.

Furthermore, after a possible fall is detected by the wireless sensor device a fall is confirmed if any of the following are further satisfied: a) a maximum value of an activity metric after a predetermined time period after the possible fall (e.g. a few seconds) is less than a threshold and a height difference measured by the altimeter before and after impact satisfies a threshold, b) a height difference measured by the altimeter before and after impact satisfies a second threshold for falling down stairs, or c) a user is lying down for $T_{lie}$ seconds and an acceleration magnitude is greater than a third threshold for falling out of bed.

As above described, the method and system allow for fall detection of a user using sensor fusion that discriminates problematic and injurious falls from activities of daily living, including but not limited to falling onto a couch to take a nap. Additionally, the fall detection can be done without regard to the attachment orientation of the wireless sensor device to the user. By implementing a tri-axial accelerometer and an altimeter within a wireless sensor device to detect acceleration and height samples and an application located within the wireless sensor device to process the detected acceleration and height samples, an efficient and cost-effective fall detection system is achieved that can support various types of falls and can confirm that the user is in a horizontal position.

A method and system for fall detection of a user using sensor fusion have been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or computer-readable medium. The software application provides instructions that enable the processor to cause the receiver to perform the functions described herein.

Furthermore, embodiments may take the form of a computer program product accessible from a computer-usable or computer-readable medium providing program code for use by or in connection with a computer or any instruction execution system. For the purposes of this description, a computer-usable or computer-readable medium can be any apparatus that can contain, store, communicate, propagate, or transport the program for use by or in connection with the instruction execution system, apparatus, or device.

The medium may be an electronic, magnetic, optical, electromagnetic, infrared, semiconductor system (or apparatus or device), or a propagation medium. Examples of a computer-readable medium include a semiconductor or solid state memory, magnetic tape, a removable computer diskette, a random access memory (RAM), a read-only memory (ROM), a rigid magnetic disk, and an optical disk. Current examples of optical disks include DVD, compact disk-read-only memory (CD-ROM), and compact disk-read/write (CD-RAN).

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for fall detection, the method comprising:
   in response to any of first and second acceleration magnitude thresholds being satisfied, determining whether a height difference before and after impact of a fall satisfies a threshold and whether an angle threshold between an acceleration vector and a calibration vector is satisfied; and determining whether a maximum value of an activity metric is less than another threshold, wherein if the maximum value of the activity metric is less than the another threshold and the height difference before and after impact satisfies the threshold, the fall detection is confirmed.

2. The method of claim 1, wherein any of first and second acceleration magnitude thresholds being satisfied further comprises:
   obtaining an acceleration sample from a user;
   comparing the acceleration sample to a first acceleration threshold;
   wherein if the acceleration sample is less than the first acceleration threshold, the first magnitude threshold is satisfied, else comparing the acceleration sample to a second acceleration threshold; and
   wherein if the acceleration sample is greater than the second acceleration threshold, the second magnitude threshold is satisfied.

3. The method of claim 2, wherein comparing the acceleration sample to the first acceleration threshold further comprises:
   applying two filters to the acceleration sample to output an acceleration vector;
   calculating $L^p$-norm of the acceleration vector to output an acceleration scalar; and
   comparing the acceleration scalar to the first acceleration threshold.

4. The method of claim 2, wherein comparing the acceleration sample to the second acceleration threshold further comprises:
   applying two filters to the acceleration sample to output an acceleration vector;
   calculating $L^p$-norm of the acceleration vector to output an acceleration scalar; and
   comparing the acceleration scalar to the second acceleration threshold.

5. The method of claim 3, wherein $L^p$-norm is any of $L^1$-norm, $L^2$-norm, $L^\infty$-norm and the two filters are any of single-pole infinite impulse response (IIR) filters, multiple-pole IIR filters, finite impulse response (FIR) filters and median filters.

6. The method of claim 4, wherein $L^p$-norm is any of $L^1$-norm, $L^2$-norm, $L^\infty$-norm and the two filters are any of single-pole infinite impulse response (IIR) filters, multiple-pole IIR filters, finite impulse response (FIR) filters and median filters.

7. The method of claim 1, wherein determining whether a maximum value of an activity metric is less than a threshold further comprises:
   after waiting a predetermined time period, applying an IIR band-pass filter to an acceleration vector of a user to produce an activity level vector of the user;
   calculating $L^1$-norm of the activity level vector to output an activity level scalar;
   calculating a moving average of the activity level scalar over a time period; and
   comparing the moving average to a predetermined activity level, wherein if the moving average is greater than the predetermined activity level, the maximum value of the activity metric is not less than the threshold and notification information of the fall detection is disregarded.

8. The method of claim 1, further comprising:
   in response to any of the first and second acceleration magnitude thresholds being satisfied, waiting a predetermined time period and determining any of whether an acceleration vector of a user is at a predetermined angle to a calibration vector and whether the user is at a stooped posture.

9. The method of claim 8, wherein determining whether an acceleration vector of the user is at a predetermined angle to a calibration vector further comprises:
   attaching a wireless sensor device to the user;
   determining the calibration vector, wherein the calibration vector is an acceleration vector when the user is vertical;
   obtaining at least one acceleration sample from the wireless sensor device;
   comparing the at least one acceleration sample to the calibration vector; and
   wherein if the at least one acceleration sample is nearly orthogonal to the calibration vector, detecting the fall of the user.

10. The method of claim 9, wherein determining the calibration vector further comprises:
    attaching a wireless sensor device when the user is vertical; and
    measuring an acceleration sample after attachment, wherein the acceleration sample is determined to be the calibration vector.

11. The method of claim 9, wherein determining the calibration vector further comprises:
    measuring an acceleration sample after the user is walking, wherein the acceleration sample is determined to be the calibration vector.

12. The method of claim 8, wherein determining whether the user is at a stooped posture further comprises:
    calculating a z-axis component of the calibration vector; and
    comparing the z-axis component of the calibration vector to a predetermined level.

13. The method of claim 1, further comprising:
    relaying notification information of the fall detection of the user to another user or device.

14. The method of claim 1, wherein the height difference is measured by an altimeter, further comprising:
    confirming a fall if any of another height difference measured by the altimeter before and after impact satisfies a first threshold for general falls, a height difference satisfies a second threshold for falling down stairs, and a user is lying down for a predetermined time period and an acceleration magnitude is greater than a threshold for falling out of bed.

15. A wireless sensor device for fall detection, the wireless sensor device comprising:
    a processing system; and
    an application to be executed by the processing system, wherein the application:
       in response to any of first and second acceleration magnitude thresholds being satisfied, determines whether a height difference before and after impact of a fall satisfies a threshold and whether an angle threshold between an acceleration vector and a calibration vector is satisfied; and
       determining whether a maximum value of an activity metric is less than another threshold, wherein if the maximum value of the activity metric is less than the another threshold and the height difference before and after impact satisfies the threshold, the fall detection is confirmed.

16. The wireless sensor device of claim 15, wherein the application further:
- determines whether an acceleration vector of a user is at a predetermined angle to a calibration vector;
- determines whether the user is at a stooped posture, and
- determines whether a maximum value of an activity metric is less than a threshold.

17. The wireless sensor device of claim 16, wherein the application determines whether any of the first and second acceleration magnitude thresholds are satisfied via an accelerometer coupled to the processing system, and wherein the application determines the height difference via an altimeter coupled to the processing system.

18. The wireless sensor device of claim 16, wherein the application determines whether a maximum value of an activity metric is less than a threshold further comprises that the application:
- after waiting a predetermined time period, applies an IIR band-pass filter to an acceleration vector of a user to produce an activity level vector of the user;
- calculates $L^1$-norm of the activity level vector to output an activity level scalar;
- calculates a moving average of the activity level scalar over a time period; and
- compares the moving average to a predetermined activity level, wherein if the moving average is greater than the predetermined activity level, the maximum value of the activity metric is not less than the threshold and notification information of the fall detection of the user is disregarded.

19. The wireless sensor device of claim 15, wherein the application further:
- relays notification information of the fall detection of a user to another user or device.

\* \* \* \* \*